United States Patent
Kudo et al.

(10) Patent No.: US 9,353,135 B2
(45) Date of Patent: May 31, 2016

(54) SILICONE COMPOUND AND A USE THEREOF

(71) Applicant: SHIN-ETSU CHEMICAL CO., LTD., Tokyo (JP)

(72) Inventors: Muneo Kudo, Annaka (JP); Shoji Ichinohe, Annaka (JP); Tomoyuki Goto, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/658,799

(22) Filed: Mar. 16, 2015

(65) Prior Publication Data

US 2015/0266905 A1  Sep. 24, 2015

(30) Foreign Application Priority Data

Mar. 20, 2014  (JP) ................................. 2014-057845

(51) Int. Cl.

| | |
|---|---|
| C08F 16/24 | (2006.01) |
| C07F 7/08 | (2006.01) |
| C07F 7/18 | (2006.01) |
| C08F 299/08 | (2006.01) |
| G02B 1/04 | (2006.01) |
| C08L 83/08 | (2006.01) |
| C08L 83/12 | (2006.01) |
| C08G 77/12 | (2006.01) |
| C08G 77/20 | (2006.01) |
| C08G 77/24 | (2006.01) |

(52) U.S. Cl.
CPC ............... *C07F 7/085* (2013.01); *C07F 7/1844* (2013.01); *C08F 299/08* (2013.01); *C08L 83/08* (2013.01); *C08L 83/12* (2013.01); *G02B 1/043* (2013.01); *C07F 7/1848* (2013.01); *C08G 77/12* (2013.01); *C08G 77/20* (2013.01); *C08G 77/24* (2013.01)

(58) Field of Classification Search
USPC .................. 526/242, 245, 246, 247
See application file for complete search history.

(56) References Cited

U.S. PATENT DOCUMENTS

| | | | |
|---|---|---|---|
| 2002/0107337 A1 | 8/2002 | Rosenzweig et al. | |
| 2008/0269429 A1 | 10/2008 | Arkles et al. | |
| 2009/0299022 A1* | 12/2009 | Ichinohe | 526/279 |
| 2012/0184696 A1* | 7/2012 | Broad et al. | 526/245 |

FOREIGN PATENT DOCUMENTS

| | | |
|---|---|---|
| JP | S59-78236 A | 5/1984 |
| JP | 2001-055446 A | 2/2001 |
| JP | 2003-516562 A | 5/2003 |
| JP | 2007-001918 A | 1/2007 |
| JP | 2007-186709 A | 7/2007 |
| JP | 2008-274278 A | 11/2008 |
| JP | 4646152 B2 | 3/2011 |
| JP | 4882136 B2 | 2/2012 |
| JP | 2013-507652 A | 3/2013 |
| WO | 01/42846 A1 | 6/2001 |
| WO | 2011/045299 A1 | 4/2011 |

* cited by examiner

*Primary Examiner* — Sudhakar Katakam
*Assistant Examiner* — Pancham Bakshi
(74) *Attorney, Agent, or Firm* — Oliff PLC

(57) ABSTRACT

One of the purposes of the present invention is to provide a compound which is a polymerizable monomer having a specific number of silicon atoms and a specific number of fluorine atoms and to provide a method for preparing the compound. The present invention provides a compound represented by the following formula (1):

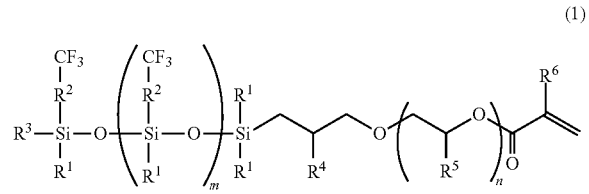

(1)

wherein m is an integer of from 2 to 10, n is an integer of from 1 to 3, $R^1$ is, independently of each other, an alkyl group having 1 to 6 carbon atoms, and $R^2$ is, independently of each other, an alkylene group having 1 to 6 carbon atoms or a fluoroalkylene group having 1 to 6 carbon atoms, $R^3$ is an alkyl group having 1 to 4 carbon atoms, and $R^4$, $R^5$ and $R^6$ are, independently of each other, a hydrogen atom or a methyl group.

12 Claims, 1 Drawing Sheet

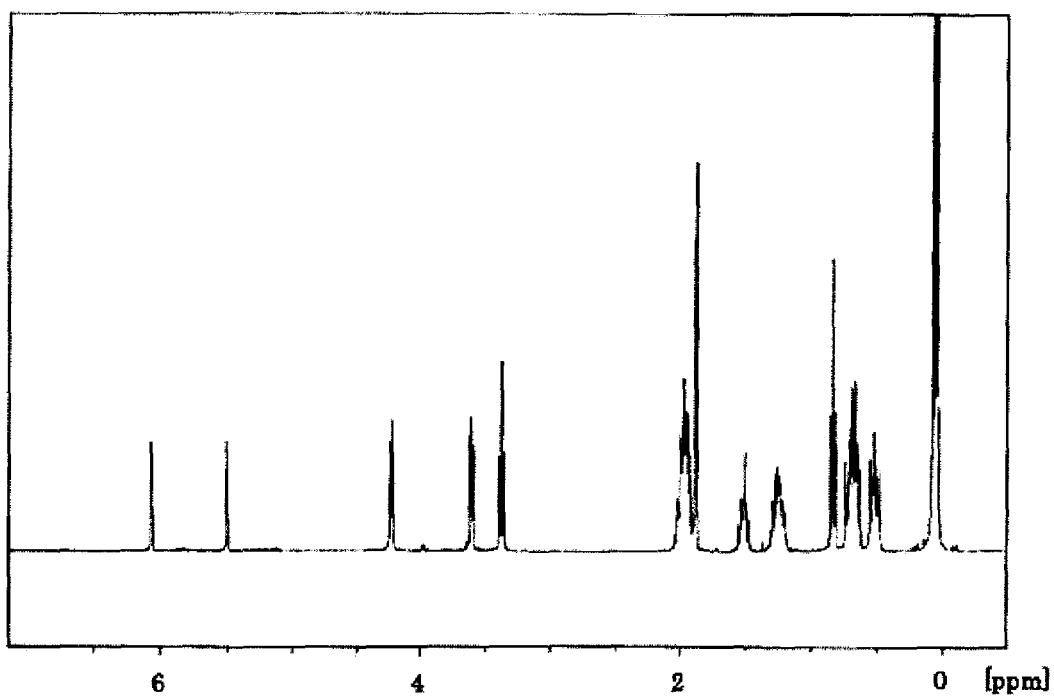

SILICONE COMPOUND AND A USE THEREOF

CROSS REFERENCE

This application claims the benefits of Japanese Patent Application No. 2014-057845 filed on Mar. 20, 2014, the contents of which are hereby incorporated by reference.

FIELD OF THE INVENTION

The present invention relates to a compound which is useful as starting materials for preparing ophthalmic devices such as contact lenses, intraocular lenses and artificial corneas, hereinafter also referred to as ophthalmic monomer, and a method for the preparation thereof. Specifically, the present invention relates to a compound which has a specific number of silicone atoms and a specific number of fluorine atoms, is copolymerizable with the other polymerizable monomer such as a (meth)acryl monomer to provide a polymer having high transparency, oxygen permeability and excellent stain resistance and being suitable for ophthalmic uses, and a method for preparing the silicone compound.

The following silicone compounds are known as an ophthalmic monomer.

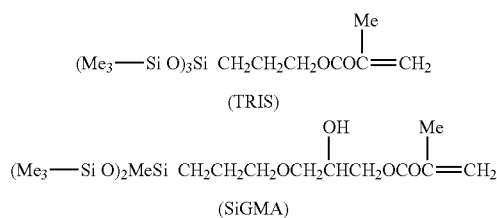

The afore-mentioned TRIS, 3-[tris(trimethylsiloxy)silyl] propyl methacrylate, has poor compatibility with hydrophilic monomers such as 2-hydroxyethyl methacrylate (HEMA). Therefore, when TRIS is copolymerized with a hydrophilic monomer, there is such a disadvantage that a transparent polymer is not obtained. In contrast, SiGMA described above has good compatibility with hydrophilic monomers such as HEMA. The copolymers obtained from SiGMA have relatively high oxygen permeability and high hydrophilicity. Recently, higher oxygen permeability is required for an ophthalmic polymer so as to be used continuously on eyes for a longer term. Polymers obtained from SiGMA do not have sufficient oxygen permeability.

In order to solve this problem, Japanese Patent Application Laid-Open No. 2007-186709, Patent Literature 1, describes a compound represented by the following formula (a).

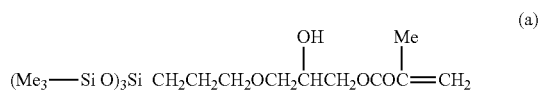

In the afore-mentioned SiGMA, the weight ratio of the Si-containing moiety, i.e. bis(trimethylsiloxy)methylsilyl, to the whole molecule is 52%. In contrast, in the aforesaid formula (a), the weight ratio of the Si-containing moiety, i.e. tris (trimethylsiloxy) silyl, to the whole molecule is 60%. The compound represented by the formula (a) thus has the higher weight ratio of the Si-containing moiety and, therefore, gives higher oxygen permeability to ophthalmic devices.

However, there is a problem such that when the weight ratio of the Si-containing moiety is increased in order to improve oxygen permeability, the mole weight of the polymerizable group became large and, therefore, strength of the copolymer decreased. Japanese Patent Application Laid-Open No. 2007-1918, Patent Literature 2, describes that the compound represented by the aforesaid formula (a) is prepared by a reaction of a corresponding epoxy precursor and methacrylic acid. There is such a problem such that many side reactions occur and the physical properties of the resulting copolymers vary.

Japanese Patent No. 4882136, Patent Literature 3, describes a compound represented by the following formula (e) and an ophthalmic lens prepared from a polymer having repeating units derived from the compound.

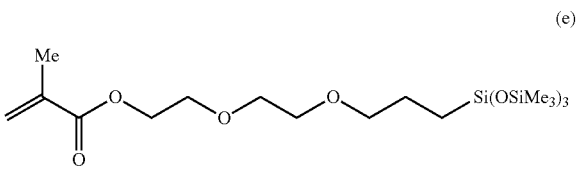

However, the polymer obtained by polymerization using the aforesaid compound as a monomer component has poor mechanical strength, and a reactivity of the polymerization of the compound is poor. Further, a stain resistance of the polymer obtained is insufficient.

It is known that a silicone having a tetrameric or more structure is thought to be preferable in term of oxygen permeability and, in particular, a silicone having a tetrameric or pentameric structure is thought to be more preferable in order to balance between oxygen permeability and strength of the copolymer. Therefore, development of a method for preparing a silicone monomer having a tetrameric or more structure with a high purity is desired.

Japanese Patent Application Laid-Open No. Sho 59-78236, Patent Literature 4, describes a method for the preparation of a silicone compound represented by a following formula (b), comprising steps of anion-polymerizing a cyclic siloxane in the presence of a lithium trialkylsilanolate as an initiator and, then, reacting the reaction product with a chlorosilane having a (meth)acryl group, such as 3-(2-methacryloyloxy ethoxy) propyl dimethyl chlorosilane.

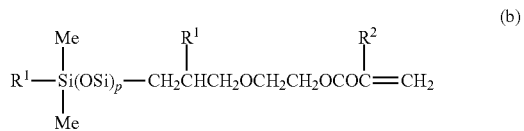

However, when the silicone compound obtained in the afore-mentioned method is mixed with a hydrophilic monomer, such as 2-hydroxyethyl methacrylate, turbidity occurs sometimes. Further, a ratio of terminals of the silicone chain blocked with the chlorosilane is not high.

Japanese Patent Application Laid-Open No. 2001-55446, Patent Literature 5, describes a method for preparing a silicone compound represented by the following formula (c) by esterifying (meth)acrylic acid or transesterifying (meth)acrylate with an organopolysiloxane having a hydroxyl group at the one terminal,

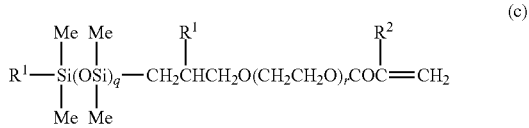

wherein r is an integer of 3 or larger.

However, the esterification ratio is insufficient, the blocked terminal ratio is low, and the compound has broad distribution of a polymerization degree of the silicone moiety.

Japanese Patent No. 4646152, Patent Literature 6, describes a method for preparing a silicone monomer represented by the following formula (d) by esterifying an organopolysiloxane having a hydroxyl group at the one terminal and a (meth)acrylic acid halide:

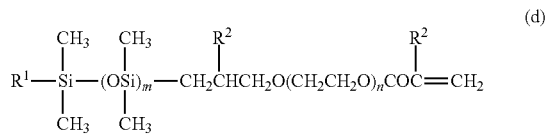

wherein m is one value out of the integers of from 3 to 10, n is one value out of 1 and 2, $R^1$ is only one out of alkyl groups having 1 to 4 carbon atoms, and $R^2$ is only one out of a hydrogen atom and a methyl group, and more than 95 weight % of the compound is one kind of compound having the specific one structure, i.e., each one value of m, n, $R^1$ and $R^2$.

A monomeric compound having a fluorinated hydrocarbon group was developed in order to increase oxygen permeability of its polymer or add stain resistance to its polymer. For instance, Japanese National Phase Publication No. 2003-516562 describes a method for copolymerizing a hydrophilic monomer, a monomer having tris(siloxysilyl) group and a monomer having a fluorinated hydrocarbon group.

Japanese Patent Application Laid-Open No. 2008-274278 and Japanese National Phase Publication No. 2013-507652 describe a fluorine-containing silicone monomer having a siloxane chain to which a fluorinated hydrocarbon group bonds as a side chain and a polymerizable group, represented by the following formula.

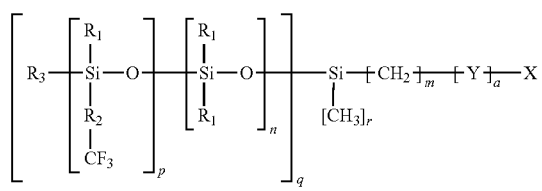

wherein X is a polymerizable group, $R_1$ is, independently of each other, an alkyl group having 1 to 6 carbon atoms or $—R_4—CF_3$, wherein $R_4$ is, independently of each other, an alkenyl group having 1 to 6 carbon atoms, $R_2$ is, independently of each other, an alkenyl group having 1 to 6 carbon atoms or a fluorine-containing alkenyl group having 1 to 6 carbon atoms, $R_3$ is a group selected from the group consisting of a monovalent linear or branched alkyl group, a siloxane chain having 1 to 30 Si—O units, a phenyl group, a benzyl group, a linear or branched hetero atom-containing group, or a combination of these, m is 1 to 6, n is 0 to 14, p is 1 to 14, a total of n and p is 15 or less, Y is a divalent connecting group, a is 0 or 1, q is 1 to 3, r is 3-q.

PRIOR LITERATURES

Patent Literature 1: Japanese Patent Application Laid-Open No. 2007-186709

Patent Literature 2: Japanese Patent Application Laid-Open No. 2007-1918

Patent Literature 3: Japanese Patent No. 4882136

Patent Literature 4: Japanese Patent Application Laid-Open No. Sho 59-78236

Patent Literature 5: Japanese Patent Application Laid-Open No. 2001-55446

Patent Literature 6: Japanese Patent No. 4646152

Patent Literature 7: Japanese National Phase Publication No. 2003-516562

Patent Literature 8: Japanese Patent Application Laid-Open No. 2008-274278

Patent Literature 9: Japanese National Phase Publication No. 2013-507652

SUMMARY OF THE INVENTION

However, the monomers described in Patent Literature 7 are less compatible with each other and the polymer obtained becomes cloudy and cause microphase separation. Further, the monomer described in Patent Literatures 8 and 9 does not have a hydrophilic group at a part bonding the (meth)acryl group and the siloxanyl group, so that the monomer is less compatible with hydrophilic monomers.

Further, Patent Literatures 8 and 9 describe that the aforesaid compound is prepared by subjecting a fluorinated hydrocarbon-containing cyclotrisiloxane to a living polymerization with alkyl lithium or lithium alkyl dimethyl silanolate as an initiator, and capping the terminal with methacryloxypropyl dimethyl chlorosilane after all of the cyclosiloxane monomer reacts. However, in the method, control of the number of siloxane repeating units having a fluorinated hydrocarbon group is difficult and, therefore, a product obtained is a mixture of compounds having various amounts of fluorine atoms. Further, the amount of fluorine atoms is too large, the compatibility between the compound and the other monomers is worse, a polymer obtained becomes cloudy and microphase separation occurs.

One of the purposes of the present invention is to provide a compound which is a polymerizable monomer having a specific number of silicon atoms and a specific number of fluorine atoms, has a higher purity, is suitable as an ophthalmic monomer, is well compatible with another (meth)acryl monomer, and provides a polymer having excellent stain resistance and to provide a method for preparing the compound.

The present inventors have made research to solve the afore-mentioned problems and found that a compound represented by the following formula (1) is well compatible with other (meth)acryl monomers and provides a colorless, transparent and excellently stain resistant polymer.

Thus, the present invention provides a compound represented by the following formula (1):

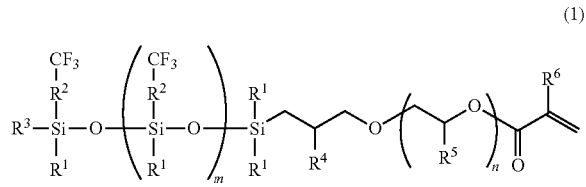

(1)

wherein m is an integer of from 2 to 10, n is an integer of from 1 to 3, $R^1$ is, independently of each other, an alkyl group having 1 to 6 carbon atoms, and $R^2$ is, independently of each other, an alkylene group having 1 to 6 carbon atoms or a fluoroalkylene group having 1 to 6 carbon atoms, $R^3$ is an alkyl group having 1 to 4 carbon atoms, and $R^4$, $R^5$ and $R^6$ are, independently of each other, a hydrogen atom or a methyl group. Further, the present invention provides a method for preparing the compound, a polymer having repeating units derived from the aforesaid compound and an ophthalmic device composed of the polymer.

EFFECTS OF THE INVENTION

The present silicone compound has higher oxygen permeability, has one kind of specific structure at a high ratio, and is well compatible with other (meth)acryl monomers to thereby provide a colorless and transparent polymer. Further, the present compound has the specific amount of fluorine atoms to thereby provide a polymer having increased stain resistance. The present method comprises a reaction of a silicone compound having a hydroxyl group and an acid chloride or an addition reaction of a silicone compound having a hydrosilyl group and a (meth)acryl compound having a terminal-unsaturated hydrocarbon group and a polyether structure. The present method provides a compound having one kind of specific structure at a high ratio. Accordingly, the present compound and the present method are useful for preparing ophthalmic devices.

BRIEF EXPLANATION OF THE DRAWING

FIG. 1 is a chart of $^1$H-NMR spectra of the silicone compound prepared in Example 1.

DETAILED DESCRIPTION OF THE INVENTION

The present silicone compound is represented by the aforesaid formula (1), which has a silicon chain structure having a fluorinated hydrocarbon side group and a hydrophilic polyether structure in the spacer part which connects a (meth)acryl structure and the siloxane structure. On account of both of the aforesaid specific structures, the present compound is well compatible with other polymerizable monomers and provides a colorless and transparent polymer having a higher oxygen permeability and an increased stain resistance.

In the aforesaid formula (1) m is an integer of from 2 to 10, preferably 3 to 7, more preferably 3. If m is smaller than the lower limit, the oxygen permeability of the polymer is worse. If m is larger than the upper limit, the hydrophilicity of the polymer is worse.

In the aforesaid formula (1), $R^5$ is, independently of each other, a hydrogen atom or a methyl group. n is an integer of from 1 to 3. The present compound has a (poly)alkyleneoxide structure to thereby has the good hydrophilicity. If n is zero, the hydrophilicity is worse. If n is larger than 3, the compound does not have one kind of a specific structure at a high ratio and a polymer thereof has poor durability and mechanical strength. Preferably, n is 1 or 2 and the silicone compound preferably has an ethylene oxide structure, an ethylene oxide-ethylene oxide structure, an ethylene oxide-propylene oxide structure or a propylene oxide-ethylene oxide structure. According to the aforesaid structure, the compound has good balance of hydrophilicity. Particularly, preferred is the compound having an ethylene oxide structure whose n is 1 and $R^5$ is a hydrogen atom. If the compound has too many propylene oxide structures, the hydrophobicity of the polymer obtained is too high and the hydrophilicity is poorer.

In the aforesaid formula (1), $R^1$ is, independently of each other, an alkyl group having 1 to 6 carbon atoms, such as a methyl group, an ethyl group, a propyl group, a butyl group, a pentyl group and a hexyl group. Among these, a methyl group is preferable.

In the aforesaid formula (1), $R^2$ is, independently of each other, an alkylene group having 1 to 6 carbon atoms or a fluoroalkylene group having 1 to 6 carbon atoms. Examples of the alkylene group include a methylene group, an ethylene group, a propylene group, a butylene group, a pentylene group and a hexylene group. Examples of the fluoroalkylene group include 2,2-difluoroethylene, 3,3-difluoropropylene, 3,3,4,4-tetrafluorobutylene, 3,3,4,4,5,5-hexafluorohexylene and 3,3,4,4,5,5,6,6-octafluorohexylene. Among these, an ethylene group is preferable.

In the aforesaid formula (1), $R^3$ is an alkyl group having 1 to 4 carbon atoms, preferably a butyl group, and $R^4$ and $R^6$ are, independently of each other, a hydrogen atom or a methyl group.

The present method of the invention provides one kind of compound which is represented by the formula (1) and has one specific structure having each specific one value of m and n at a high ratio, as will described below. A high ratio means that an amount of the aforesaid one kind of compound having an each specific one value of m and n, based on a total amounts of the compound represented by the formula (1), is more than 95 mass %, preferably 97 mass % or more, further preferably 99 mass % or more. One kind of compound having one specific structure is particularly a compound having an each specific one value of $R^1$, $R^2$, $R^3$, $R^4$, $R^5$ and $R^6$ and a specific one kind of (poly)alkyleneoxide structure. In the present invention, the ratio is determined in gas chromatography, hereinafter referred to as "GC". The details of GC will be described below. When the compound is mixed with a non-silicone monomer such as 2-hydroxyethyl methacrylate, any turbidity does not occur and a transparent polymer is obtained, because the starting compound has a high ratio of one specific structure. If the ratio is less than 95 mass %, for instance, other compounds having different values of m are contained in an amount of more than 5 mass %, a mixture of the present silicone compound and a non-silicone monomer is turbid and does not provide a colorless and transparent polymer.

When m is 3, n is 1, $R^1$ is a methyl group, $R^2$ is an ethylene group, $R^3$ is a butyl group, $R^4$ and $R^5$ are each a hydrogen atom and $R^6$ is a methyl group in the formula (1), the molecular weight is 910 and a content of siloxanes is approximately 50 mass %, based on the total mass of the compound other than the fluoromethyl group and a content of fluorine atoms is approximately 25 mass %, based on the total mass of the compound. That is, the compound comprises a large amount of Si atoms, whereby a polymer obtained therefrom has high oxygen permeability. Further, the compound has a desired amount of a fluorine atom and, therefore, stain resistance of a polymer is improved.

The present invention further provides methods for preparing the afore-mentioned compound represented by the formula (1).

One of the present methods comprises a step of reacting a silicone compound represented by the following formula (2):

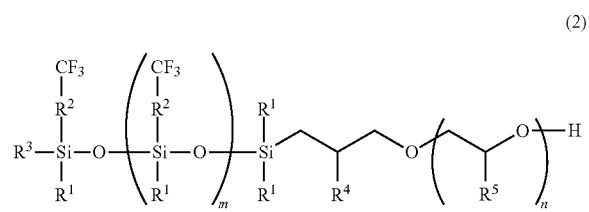

(2)

wherein m, n, $R^1$, $R^2$, $R^3$, $R^4$ and $R^5$ are as defined above; with (meth)acryl acid halide represented by the following formula (3):

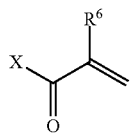

(3)

wherein X is a Cl, Br or I atom and $R^6$ is as defined above. The reaction is preferably carried out in such a manner that the acid halide represented by the formula (3), preferably an acid chloride, is slowly added to a solution of the polyorganosiloxane represented by the formula (2) in toluene or hexane to be allowed to react at a temperature of from 0 to 50 degrees C. under cooling, for instance, in a water bath.

The amount of the acid halide (3) is 1 to 3 moles, preferably 1.05 to 2 moles, per mole of the polyorganosiloxane represented by the formula (2). If the amount is smaller than the lower limit, the polyorganosiloxane (2) would remain unreacted in the reaction product and a high ratio of one specific structure of the formula (1) is not attained. If the amount is larger than the upper limit, this is economically disadvantageous.

The aforesaid reaction is preferably carried out in the presence of an acid scavenger. On account of the acid scavenger, a higher yield is obtained. Examples of the acid scavenger include amines such as triethylamine and pyridine, preferably triethylamine. An amount of the acid scavenger may be 1 mole to 2 moles, per mole of the (meth)acryl acid halide represented by the formula (3).

A purity of the (meth)acryl acid halide have an influence on a ratio of one specific compound in the silicone compound represented by the formula (1). The (meth)acryl acid halide preferably has a higher purity. In particular, commercial (meth)acryl acid halide having a purity of 99% or more is preferable. Almost no side reaction occurs in the reaction with an acid chloride.

A preferred embodiment in the present method is such that a peak of the unreacted silicone compound represented by the formula (2) is monitored in GC during the reaction; and after disappearance of the peak is confirmed in GC, water is added to the reaction mixture and stirred. Then, the reaction mixture is left standing to cause phase separation into an aqueous phase and an organic phase. The organic phase is washed with water several times and, then, a solvent in the organic phase is stripped off. According to this manner, a compound having one specific structure at more than 95 mass % in GC is obtained. The ratio is decided by a percentage area of the peak in GC. When a flame ionization detector (FID) is used, an area of the peak is proportional to the number of its carbon atoms. Therefore, a percentage area is almost equal to its mass percentage.

The silicone compound represented by the aforesaid formula (2) is prepared by an addition reaction of a polyorganohydrogen siloxane represented by the following formula (4):

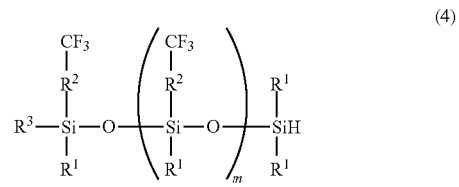

(4)

wherein m, $R^1$, $R^2$ and $R^3$ are as defined above; with a compound represented by the following formula (5), hereinafter referred to as "allyl ether compound":

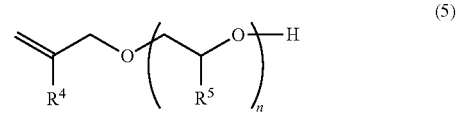

(5)

wherein n, $R^4$ and $R^5$ are as defined above.

This addition reaction may be carried out in any conventional manners. For instance, the reaction is carried out in the presence of a hydrosilylation catalyst such as platinum group metal compounds. A solvent may be used. Examples of the solvent include aliphatic or aromatic solvents such as hexane, methylcyclohexane, ethylcyclohexane and toluene; and alcoholic solvents such as ethanol and IPA. A ratio of the aforesaid compounds to be used may be according to conventional manners. The amount of the allyl ether compound may be 1.2 moles or more, preferably 1.5 moles or more, per mole of the polyorganohydrogen siloxane. The upper limit of the amount may be usually 5 moles or less, particularly 3 moles or less, but is not limited to them.

The allyl ether compound represented by the aforesaid formula (5) is preferably represented by the following formulas.

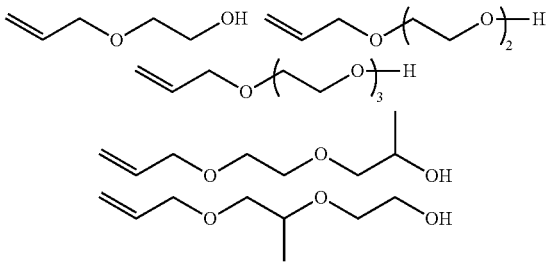

It is preferred that the ally ether compound is optionally diluted with a solvent to which, then, a hydrosilylation catalyst of platinum family is added. Any conventional hydrosilylation catalysts of platinum family may be used and not limited to any particular one. Subsequently, the polyorganohydrogen siloxane is added dropwise to the mixture to react at room temperature or a higher temperature. After the completion of the addition, the reaction mixture is held under heating, until disappearance of the peak of the raw material, polyorganohydrogensiloxane, is confirmed, for instance, in GC. After the end point of the reaction is confirmed in GC, the unreacted polyorganohydrogen siloxane does not remain in a product, so that a silicone compound obtained has one specific structure at a higher ratio. The aforesaid addition reaction may be conducted in one step.

After the completion of the addition reaction, an excessive allyl ether compound is removed from the reaction liquid. For instance, the reaction liquid is subjected to stripping under a reduced pressure, or washed with ion exchanged water or an aqueous sodium sulfate solution to extract the allyl ether compound into an aqueous phase. Here, a proper amount of solvent, such as toluene and hexane, may preferably be used to attain clear phase separation. In particular, the solvent is stripped off from the organic phase under a reduced pressure, whereby the silicone compound represented by the aforesaid formula (2) and having a high ratio of one specific structure such as more than 95 mass %, even approximately 97 mass % or more, further approximately 99 mass % or more, is obtained. The silicone compound may be distilled twice or more to further increase the ratio. A high ratio means that an amount of the aforesaid one kind of compound having each specific one value of m and n, based on a total amounts of the compound represented by the formula (2), is more than 95 mass %, preferably 97 mass % or more, further preferably 99 mass % or more. The one specific structure means one kind of compound having each one value of m and n, particularly, one kind of compound having each one value of m, n, $R^1$, $R^2$, $R^3$ and $R^4$ and one kind of (poly)alkylene oxide structure.

The polyorganohydrogen siloxane represented by the aforesaid formula (4) may be prepared in known manners. For instance, the compound (4) wherein m is 3, $R^1$ is a methyl group, $R^2$ is an ethylene group and $R^3$ is a butyl group may be prepared in the following manner. First, $BuMe(CF_3CH_2CH_2)SiOLi$ is synthesized using BuLi. 1,3,5-Tris(3,3,3-trifluoropropyl)-1,3,5-trimethylcyclo trisiloxane is subjected to a ring-opening reaction using the $BuMe(CF_3CH_2CH_2)SiOLi$ as an initiator and, then, the reaction is terminated with dimethylchlorosilane. Thus, a mixture of compounds having m of 2 to 5 is obtained. The mixture is distillated to collect a fraction at 146 degrees C. and 84 Pa to obtain a compound whose m is 3, at a ratio of 98 mass % or higher in the fraction obtained. Alternatively, the distillation may be carried out after the mixture is addition reacted with the allyl ether compound represented by the formula (5). However, the product of the addition reaction has a higher boiling point. Therefore, the former manner is preferred. Then, a silicone compound (2) having one specific structure is obtained at a higher ratio.

The silicone compound (2) may be prepared also by the steps of subjecting the allyl ether to a silylation to provide a silyl ester with a silylating agent such as hexamethyldisilazane, addition reacting the compound obtained in the aforesaid manners and, then, hydrolyzing the silyl ester.

Another method of the present methods for preparing the aforesaid formula (1) comprises a step of reacting a polyorganohydrogen siloxane represented by the following formula (4):

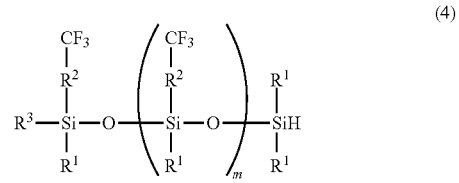

wherein m, $R^1$, $R^2$ and $R^3$ are as defined above;
with a compound represented by the following formula (6):

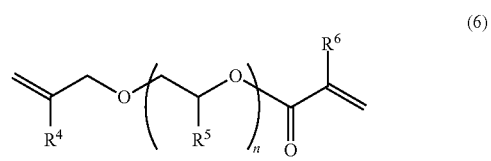

wherein n, $R^4$ and $R^5$ are as defined above.

This addition reaction may be carried out in any conventional manners. For instance, the reaction is carried out in the presence of a hydrosilylation catalyst such as platinum group metal compounds. A solvent may be used. Examples of the solvent include aliphatic or aromatic solvents such as hexane, methylcyclohexane, ethylcyclohexane and toluene; and alcoholic solvents such as ethanol and IPA. The amount of the compound represented by the formula (6) may be 1.2 moles or more, preferably 1.5 moles or more, per mole of the polyorganohydrogen siloxane. The upper limit of the amount may be usually 5 moles or less, particularly 3 moles or less, but is not limited to them.

The compound represented by the aforesaid formula (6) is preferably these represented by the following formulas.

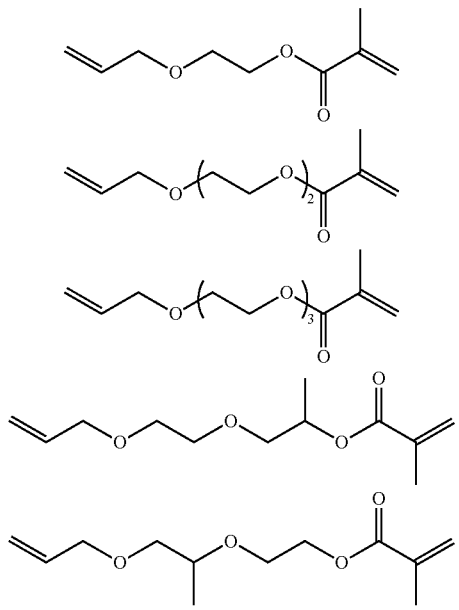

It is preferred that the compound represented by the formula (6) is optionally diluted with a solvent to which, then, a hydrosilylation catalyst of platinum family is added. Any conventional hydrosilylation catalysts of platinum family may be used and not limited to any particular one. Subsequently, the polyorganohydrogen siloxane is added dropwise to the mixture to react at room temperature or a higher temperature. After the completion of the addition, the reaction mixture is held under heating, until disappearance of the peak of the raw material, polyorganohydrogen siloxane, is confirmed, for instance, in GC. After the endpoint of the reaction is confirmed in GC, the unreacted polyorganohydrogen siloxane does not remain in a product, so that a silicone compound obtained has one specific structure at a higher ratio. The aforesaid addition reaction may be conducted in one step.

After the completion of the addition reaction, an excessive amount of the compound represented by the formula (6) is removed from the reaction liquid. For instance, the reaction liquid is subjected to stripping under a reduced pressure, or washed with ion exchanged water or an aqueous sodium sulfate solution to extract the compound represented by the formula (6) into an aqueous phase. Here, a proper amount of solvent, such as toluene and hexane, may preferably be used to attain clear phase separation. In particular, the compound represented by the formula (6) is stripped off from the reaction product under a reduced pressure, whereby the silicone compound represented by the aforesaid formula (1) and having a high ratio of one specific structure such as more than 95 mass %, even approximately 97 mass % or more, further approximately 99 mass % or more, is obtained.

The silicone compound of the present invention is well compatible with other compounds having a group polymerizable with the silicone compounds, such as compounds having a (meth)acryl group, hereinafter referred to as "polymerizable monomer". Therefore, the silicone compound copolymerizes with the polymerizable monomer to provide a colorless and transparent polymer. The silicone compound has a fluorinated hydrocarbon atom, so that it provides a polymer having excellent stain resistance. Further, the silicone compound is well compatible with a fluorinated substituent group-containing (meth)acryl monomer, so that stain resistance of the polymer obtained is increased.

Examples of the polymerizable monomer include acryl monomers such as (meth)acrylic acid, methyl(meth)acrylate, ethyl(meth)acrylate, (poly)ethylene glycol dimethacrylate, polyalkylene glycol mono(meth)acrylate, polyalkylene glycol monoalkyl ether(meth)acrylate, trifluoroethyl(meth)acrylate, 2-hydroxyethyl(meth)acrylate, and 2,3-dihydroxypropyl(meth)acrylate; acrylic acid derivatives such as N,N-dimethyl acrylamide, N,N-diethyl acrylamide, N-acryloyl morpholine, and N-methyl(meth)acrylamide; other ethylenically unsaturated aliphatic or aromatic compound such as crotonic acid, cinnamic acid, and vinyl benzoic acid; and silicone compounds having polymerizable groups such as a (meth)acryl group. These may be used singly or two or more of them may be used in combination.

The copolymerization of the present compound and the other polymerizable monomer mentioned just above may be carried out in conventional known manners. For instance, known polymerization initiator such as thermal polymerization initiators or photo polymerization initiators may be used. Examples of the polymerization initiator include 2-hydroxy-2-methyl-1-phenyl-propane-1-one, azobis isobutyronitrile, azobis dimethylvaleronitrile, benzoyl peroxide, tert-butyl hydroperoxide, and cumene hydroperoxide. The polymerization initiator may be used singly or two or more of them may be used in combination. The amount of the polymerization initiator is 0.001 to 2 parts by mass, preferably 0.01 to 1 part by mass, relative to 100 parts by mass of a total amount of the polymerizable components.

A polymer having a unit derived from the compound in the present invention has high oxygen permeability and excellent durability of mechanical strength in a buffered phosphate solution and stain resistance. Therefore, the present compounds are suitable as materials for preparing ophthalmic devices such as contact lenses, intraocular lenses and artificial corneas. A method for preparation of the ophthalmic device with the present polymer may be any conventional ones. For instance, a machining method and a molding method may be used for forming lenses such as contact lenses and intraocular lenses.

EXAMPLES

The present invention will be explained below in further detail with reference to a series of the Examples and the Comparative Examples, though the present invention is in no way limited by these Examples.

In the following descriptions, a viscosity was determined by a Cannon-Fenske viscosimeter and a specific gravity was as determined by a hydrometer. A refraction index was as determined by a digital refractometer RX-5000, ex Atago Co., Ltd. $^1$H-NMR analysis was conducted by JNM-ECP500, ex JEOL Ltd. with deuterochloroform as a measuring solvent. A ratio of a compound was determined by gas chromatography, i.e. GC. Conditions in GC were as follows.

[GC Conditions]
Gas chromatograph: ex Agilent Technologies, Inc.
Detector: FID, temperature of 300 degrees C.
Capillary Column: HP-5MS (0.25 mm×30 m×0.25 micrometer), ex J & W
Temperature rise program: 50 degrees C. for 5 minutes, 10 degrees C./minute and, then, maintained at 250 degrees C.
Temperature at an inlet: 250 degrees C.
Carrier gas: Helium with a flow rate of 1.0 ml/minute
Split ratio: 50:1
Injection volume: 1 microliter Synthesis Example 1

In a three-liter flask equipped with a stirring device, a dimroth condenser, a thermometer and a dropping funnel, put were 112.4 g (0.24 mol) of 1,3,5-tris(3,3,3-trifluoropropyl)-1,3,5-trimethylcyclo trisiloxane and 60 g of toluene, and cooled to an internal temperature of 0 degrees C. Then, 450 ml (0.72 mol) of a 1.6 M solution of n-butyllithium was added dropwise in the flask over two hours at the internal temperature of 0 to 15 degrees C. The reaction mixture was held at 15 degrees C. for one hour, to which a mixture of 337.4 g (0.72 mol) of 1,3,5-tris(3,3,3-trifluoropropyl)-1,3,5-trimethylcyclo trisiloxane and 270 g of tetrahydrofuran was then added dropwise over two hours at the internal temperature of 0 to 5 degrees C. The reaction mixture was aged at the internal temperature of 0 to 5 degrees C. for two hours and, then, further at the internal temperature of 20 to 25 degrees C. for one hour. 7.3 g (0.72 mol) of triethylamine was added to the reaction mixture and, then, 88.6 g (0.94 mol) of dimethyldichlorosilane was added dropwise in the flask over two hours at the internal temperature of 20 to 25 degrees C. The reaction mixture was aged at the internal temperature of 20 to 25 degrees C. for one hour. 1000 Grams of water were added to the reaction mixture, stirred for 5 minutes and, then, left standing to cause phase separation. The aqueous phase was discarded. The solvent in the organic phase was distilled off under a reduced pressure to obtain 526 g of a mixture comprising 57.1% of the desired compound. The mixture was distillated to collect a fraction at 146 degrees C. and 84 Pa to obtain 255 g of a product with a yield of 47.8% (0.34 mol). $^1$H-NMR analysis showed that the product was a compound represented by the following formula (7). The ratio of the compound represented by the following formula (7) in the obtained product was 98.4 mass %, as determined in GC, the viscosity was 11 mm²/s at 25 degrees C., the specific gravity was 1.144 at 25 degrees C. and the refraction index was 1.3810.

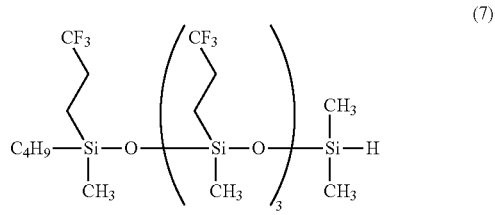

(7)

Example 1

In a one-liter flask equipped with a stirring device, a dimroth condenser, a thermometer and a dropping funnel, put were 38.25 g (0.375 mol) of ethylene glycol monoallyl ether represented by the following formula (8) and 100 g of toluene, and heated to 70 degrees C. 0.38 Gram of a solution of a catalyst, complex of alkali-neutralized chloroplatinic acid with vinyl siloxane, in toluene, containing 0.5% of platinum, was added in the flask. Then, 185 g (0.25 mol) of the compound represented by the aforesaid formula (7) was added dropwise in the flask with the dropping funnel over one hour. The reaction mixture was held at 100 degrees C. for one hour and, then, analyzed in GC. The peak of the compound represented by the aforesaid formula (7) disappeared, which means that the reaction completed. 100 Grams of ion exchanged water were added to the reaction mixture with stirring to wash it and, then, left standing to cause phase separation. The aqueous phase containing the excessive ethylene glycol monoallyl ether was removed. The organic phase was similarly washed twice with each 100 g of ion exchanged water and, then, the toluene in the organic phase was stripped off under a reduced pressure to obtain 193.7 g (0.23 mol) of a colorless and transparent liquid, silicone compound represented by the following formula (9). The yield was 92%. The ratio of the silicone compound represented by the following formula (9) in the obtained product was 98.1 mass %, as determined in GC.

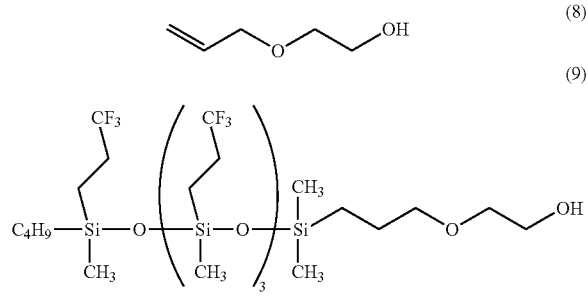

(8)

(9)

In a one-liter flask equipped with a stirring device, a dimroth condenser, a thermometer and a dropping funnel, put were 168.4 g (0.2 mol) of the silicone compound represented by the aforesaid formula (9), 25.3 g (0.25 mol) of triethylamine as a dehydrochlorination agent, and 250 g of hexane. Then, a mixture of 23.6 g (0.23 mol) of methacrylic acid chloride and 25 g of hexane was added dropwise over one hour, while cooling the flask in a water bath. The internal temperature rose from 20 degrees C. up to 30 degrees C. The water bath was removed and the reaction mixture was held at room temperature, while monitoring the peak of the silicone compound represented by the formula (9) in GC. Ten hours later, the intensity of the peak of the silicone compound fell down below the detection limit by GC and, then, 250 g of ion exchanged water was added to the reaction mixture to wash it. The reaction mixture was left standing to cause phase separation. The aqueous phase was discarded. The organic phase was washed twice with water. The solvent, hexane, was stripped off from the organic phase under a reduced pressure to obtain 163.8 g (0.18 mol) of a colorless and transparent liquid product with a yield of 90%. ¹H-NMR analysis showed that the obtained compound in the product was a silicone compound represented by the following formula (10), hereinafter referred to as silicone compound 1. The ratio of the silicone compound represented by the following formula (10) in the product was 97.8 mass %, as determined in GC, the viscosity was 21.6 mm²/s at 25 degrees C., the specific gravity was 1.139 at 25 degrees C. and the refraction index was 1.4037.

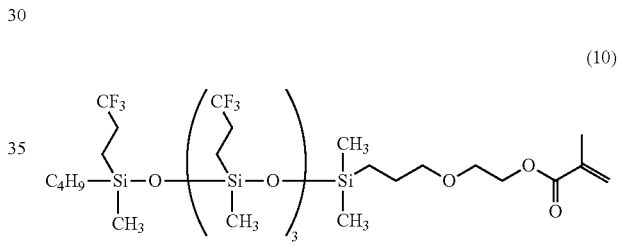

(10)

Example 2

In a one-liter flask equipped with a stirring device, a dimroth condenser, a thermometer and a dropping funnel, put were 54.4 g (0.32 mol) of a compound represented by the following formula (11) and 100 g of metylcyclohexane, and heated to 70 degrees C. 0.15 Gram of a solution of a catalyst, complex of alkali-neutralized chloroplatinic acid with vinyl siloxane, in toluene, containing 0.5% of platinum, was added in the flask. Then, 148 g (0.2 mol) of the compound represented by the aforesaid formula (7) was added dropwise in the flask with the dropping funnel over one hour. The reaction mixture was held at 100 degrees C. for one hour and, then, analyzed in GC. The peak of the compound represented by the aforesaid formula (7) disappeared, which means that the reaction completed. Methylcyclohexane was stripped off under a reduced pressure to obtain 174.7 g (0.19 mol) of a colorless and transparent liquid with a yield of 96%. ¹H-NMR analysis showed that the obtained compound in the product was a silicone compound represented by the aforesaid formula (10). The ratio of the silicone compound represented by the aforesaid formula (10) in the obtained product was 98.0 mass %, as determined in GC, the viscosity was 21.6 mm²/s at 25 degrees C., the specific gravity was 1.139 at 25 degrees C. and the refraction index was 1.4037.

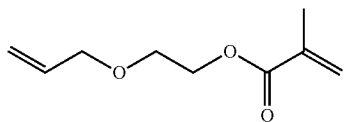

(11)

Comparative Synthesis Example 2

The procedures of Example 9 described in Japanese Patent Application Laid-Open No. 2008-274278, Patent Literature 8, were repeated to synthesize a polysiloxane represented by the following formula (12). The obtained product was a mixture of a compound whose m was 0, a compound whose m was 3, a compound whose m was 6, and a compound whose m was 9, hereinafter referred to as silicone compound 2.

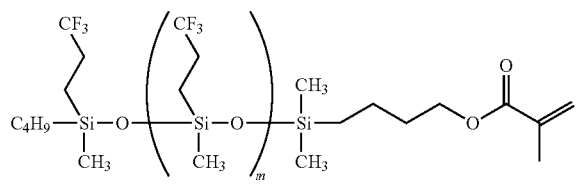

(12)

Comparative Synthesis Example 2

The procedures of Example 1 described in Japanese Patent No. 4646152, Patent Literature 6, were repeated to synthesize a compound represented by the following formula (13), hereinafter referred to as silicone compound 3.

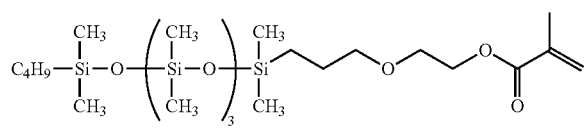

(13)

The obtained compound was a colorless and transparent liquid. The ratio of the silicone compound represented by the aforesaid formula (13) in the obtained product was 98.3 mass %, as determined in GC.

Comparative Synthesis Example 4

The procedures of Example 2 were repeated, except that 40.3 g (0.32 mol) of allyl methacrylate was used instead of 54.4 g (0.32 mol) of the compound represented by the aforesaid formula (11) to obtain 165.3 g (0.194 mol) of a colorless and transparent liquid product with a yield of 97%. ¹H-NMR analysis showed that the obtained compound in the product was a silicone compound represented by the following formula (14), hereinafter referred to as silicone compound 4. The ratio of the silicone compound represented by the formula (14) in the obtained product was 98.7 mass %, as determined in GC, the viscosity was 18.4 mm²/s at 25 degrees C., the specific gravity was 1.143 at 25 degrees C. and the refraction index was 1.4046.

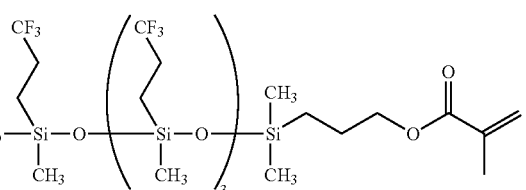

(14)

Preparation of a Monomer Mixture

Example 3

60 Parts by mass of silicone compound 1 prepared in Example 1, 35 parts by mass of N,N-dimethyl acryl amide, 1 part by mass of triethylene glycol dimethacrylate, 5 parts by mass of trifluoroethyl methacrylate and 0.5 part by mass of Darocur 1173, ex Ciba Specialty Chemicals Inc., were mixed with stirring to obtain monomer mixture 1.

Example 4

60 Parts by mass of silicone compound 1 prepared in Example 1, 40 parts by mass of N,N-dimethyl acryl amide, 1 part by mass of triethylene glycol dimethacrylate and 0.5 part by mass of Darocur 1173, ex Ciba Specialty Chemicals Inc., were mixed with stirring to obtain monomer mixture 2.

Comparative Examples 1 to 3

In Comparative Example 1, the same components and the same manners as in Example 3 were used, except that silicone compound 2 prepared in Synthesis Example 2 was used instead of silicone compound 1 to obtain a monomer mixture, hereinafter referred to as monomer mixture 3.

In Comparative Example 2, the same components and the same manners as in Example 3 were used, except that silicone compound 3 prepared in Synthesis Example 3 was used instead of silicone compound 1 to obtain a monomer mixture, hereinafter referred to as monomer mixture 4.

In Comparative Example 3, the same components and the same manners as in Example 3 were used, except that silicone compound 4 prepared in Synthesis Example 4, was used instead of silicone compound 1 to obtain a monomer mixture, hereinafter referred to as monomer mixture 5.
[Evaluations]
(1) Compatibility with Other Polymerizable Monomers The appearances of the monomer mixtures obtained were observed visually. A mixture comprising a silicone compound having good compatibility with the other (meth)acryl compounds was colorless and transparent. In contrast, a mixture comprising a silicone compound having bad compatibility with the other (meth)acryl compounds was turbid. The results are as shown in Table 1.

(2) Appearance of a Film, Composed of the Polymer

The each mixture was deaerated in an argon atmosphere. The mixture obtained was poured into a mold having two pieces of quartz glass plates which faced each other. The mixture was irradiated with light from an extra high pressure mercury lamp for one hour to obtain a film having a thickness of approximately 0.3 mm. The appearance of the film was observed visually. The results are as shown in Table 1.

(3) Water Wettability, or Hydrophilicity, of a Film Surface, Composed of the Polymer Water contact angles of the films prepared in (2) above were determined by a liquid drop method with a contact angle meter CA-D type, ex Kyowa Interface Science Co., LTD. The results are as shown in Table 1.

(4) Stain Resistance of a Film, Composed of the Polymer

Two films for each one mixture were prepared in the same manner as in (2) above. One of the twos was soaked in a buffered phosphate solution, PBS(−), at 37 degrees C. for 24 hours. The film after soaked and another film without being soaked were stored in a well-known artificial lipid solution at 37 plus-minus 2 degrees C. for 8 hours. Then, the films were washed with PBS(−) and, subsequently, soaked in a 0.1% solution of sudan black sesame oil. When the colors were not different between the film after soaked and the film without being soaked, the film was evaluated as "good". When the color of the film after soaked was different between the film without being soaked, that is, the film was stained with the sudan black sesame oil, the film was evaluated as "bad". The results are as shown in Table 1.

(5) Durability of Mechanical Strength of a Film, Composed of the Polymer

Two films for each one mixture were prepared in the same manner as in 2) above. Any water on the surface of the films was wiped off. Then, one of the twos was soaked in a buffered phosphate solution, PBS(−), at 37 degrees C. for 24 hours. The film after soaked and another film without being soaked were cut into test samples having a dumbbell shape of a width of 2.0 mm. The top and the bottom of the test sample was held by a jig and pulled at a constant speed. Tensile strength and elongation at break were determined with a tensile tester AGS-50NJ, ex Shimadzu Corporation. When a change of the value of the tensile strength or the rupture elongation of the film after soaked, relative to the value of the film without being soaked was not larger than 10%, it was evaluated as "good". When a change of the value of the tensile strength or the rupture elongation of the film after soaked, relative to the value of the film without being soaked was larger than 10%, it was evaluated as "bad". The results are as shown in Table 1.

TABLE 1

|  | Example 3 | Example 4 | Comparative Example 1 | Comparative Example 2 | Comparative Example 3 |
|---|---|---|---|---|---|
| Monomer mixture | 1 | 2 | 3 | 4 | 5 |
| (1) Compatibility | Colorless and transparent | Colorless and transparent | Turbid | Slightly turbid | Slightly turbid |
| (2) Appearance of the film | Colorless and transparent | Colorless and transparent | Cloudy | Slightly cloudy | Slightly cloudy |
| (3) Water contact angle, ° | 49 | 47 | 59 | 64 | 53 |
| (4) Stain resistance | Good | Good | Bad | Bad | Bad |
| (5) Durability of a mechanical strength | Good | Good | Bad | Bad | Bad |

The compounds used in Comparative Examples 1 and 3 were less compatible with the other (meth)acryl monomers and did not provide a colorless and transparent polymer. The compound used in Comparative Example 2 did not have any fluorinated hydrocarbon group and, therefore, was less compatible with trifluoroethyl(meth)acrylate and did not provide a colorless and transparent polymer. Further, the polymers obtained from the monomer mixtures in Comparative Examples 1 to 3 had poor water wettability (hydrophilicity), stain resistance and durability of mechanical strength. In contrast, the silicone compound of the present invention is well compatible with the other (meth)acryl monomer and provides a colorless and transparent polymer. Further, the silicone compound is well compatible with a fluorinated (meth)acryl monomer, too. Therefore, the silicone compound provides a polymer having excellent water wettability, stain resistance and durability of mechanical strength. Further, as shown in Example 4 of Table 1, the present silicone compound provides, on account of its fluorinated hydrocarbon group, a polymer having an excellent stain resistance without other fluorinated monomer.

INDUSTRIAL APPLICABILITY

The present silicone compound provides a polymer having excellent hydrophilicity, stain resistance and durability of mechanical strength. Further, the present method provides a compound having one specific structure at a high ratio.

Accordingly, the present compound and the present method are useful for preparing ophthalmic devices such as contact lenses, intraocular lenses and artificial corneas.

The invention claimed is:

1. A compound mixture having the following formula (1):

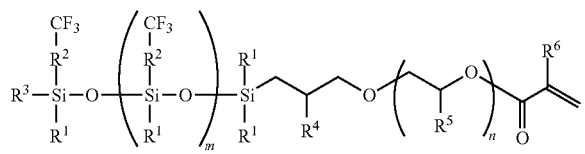

wherein m is an integer of from 2 to 10, n is an integer of from 1 to 3, $R^1$ is, independently of each other, an alkyl group having 1 to 6 carbon atoms, $R^2$ is, independently of each other, an alkylene group having 1 to 6 carbon atoms or a fluoroalkylene group having 1 to 6 carbon atoms, $R^3$ is an alkyl group having 1 to 4 carbon atoms, and $R^4$, $R^5$ and $R^6$ are, independently of each other, a hydrogen atom or a methyl group, wherein more than 95 mass % of a total mass of the compound mixture having the formula (1) consists of a structure having a single value for m and a single value for n in the formula (1).

2. The compound mixture according to claim 1, wherein m in the formula (1) is 3.

3. A polymer having repeating units derived from the compound mixture according to claim 1 and repeating units derived from at least one other compound having a group which is polymerizable with said compound.

4. An ophthalmic device composed of the polymer according to claim 3.

5. A method for preparing the compound of claim 1 having the following formula (1):

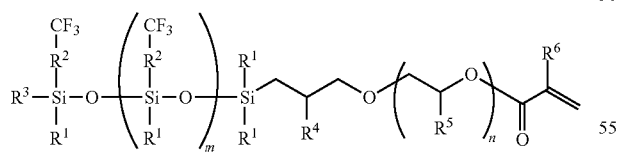

wherein m is an integer of from 2 to 10, n is an integer of from 1 to 3, $R^1$ is, independently of each other, an alkyl group having 1 to 6 carbon atoms, $R^2$ is, independently of each other, an alkylene group having 1 to 6 carbon atoms or a fluoroalkylene group having 1 to 6 carbon atoms, $R^3$ is an alkyl group having 1 to 4 carbon atoms, and $R^4$, $R^5$ and $R^6$ are, independently of each other, a hydrogen atom or a methyl group, comprising a step of reacting a silicone compound having the following formula (2):

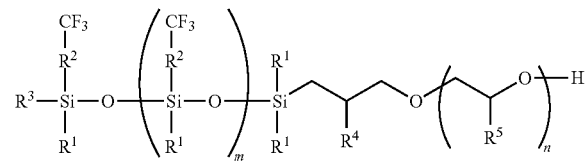

wherein m, n, $R^1$, $R^2$, $R^3$, $R^4$ and $R^5$ are as defined above;

with a (meth)acryl acid halide having the following formula (3):

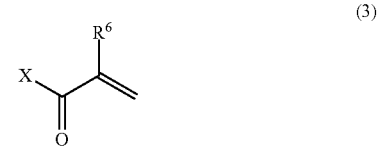

wherein X is a Cl, Br or I atom and $R^6$ is as defined above.

6. The method according to claim 5, wherein said reaction is carried out in the presence of an acid scavenger.

7. The method according to claim 6, wherein the acid scavenger is triethylamine.

8. The method according to claim 5, wherein the method comprises a step of reacting a polyorganohydrogen siloxane having the following formula (4):

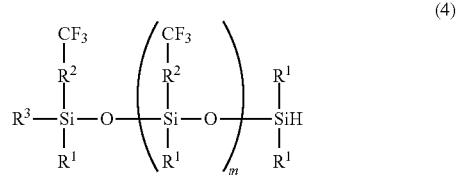

wherein m, $R^1$, $R^2$ and $R^3$ are as defined above;

with a compound having the following formula (5):

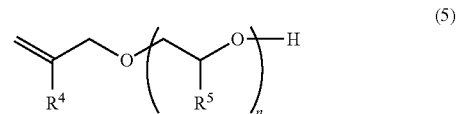

wherein n, $R^4$ and $R^5$ are as defined above;

to thereby prepare the silicone compound having the aforesaid formula (2).

9. The method according to claim 8, wherein an amount of one kind of compound having each one value of m and n in the formula (2) is more than 95 mass % of a total mass of the compound.

10. A method for preparing a compound having the following formula (1):

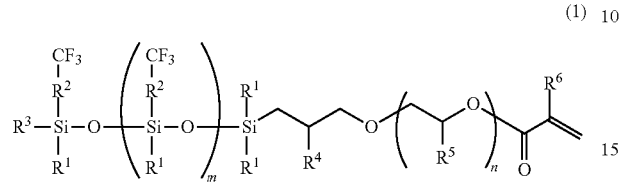
(1)

wherein m is an integer of from 2 to 10, n is an integer of from 1 to 3, $R^1$ is, independently of each other, an alkyl group having 1 to 6 carbon atoms, $R^2$ is, independently of each other, an alkylene group having 1 to 6 carbon atoms or a fluoroalkylene group having 1 to 6 carbon atoms, $R^3$ is an alkyl group having 1 to 4 carbon atoms, and $R^4$, $R^5$ and $R^6$ are, independently of each other, a hydrogen atom or a methyl group, comprising a step of reacting a polyorganohydrogen siloxane having the following formula (4):

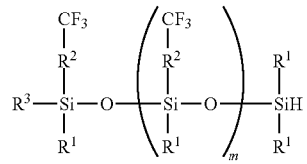
(4)

wherein m, $R^1$, $R^2$ and $R^3$ are as defined above;
with a compound having the following formula (6):

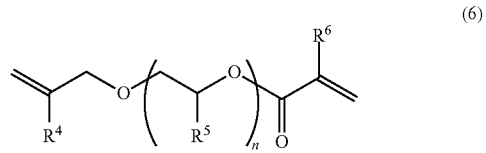
(6)

wherein n, $R^4$ and $R^5$ are as defined above.

11. The method according to claim 5, wherein an amount of one kind of compound having each one value of m and n in the formula (1) is more than 95 mass % of a total mass of the compound.

12. The method according to claim 5, wherein m in the formula (1) is 3.

* * * * *